United States Patent
Bordusa et al.

(10) Patent No.: US 7,459,526 B2
(45) Date of Patent: Dec. 2, 2008

(54) METHOD FOR SYNTHESIZING PEPTIDES, PEPTIDE MIMETICS AND PROTEINS

(75) Inventors: Frank Bordusa, Rossbach (DE); Hans-Dieter Jakubke, Dresden-Langebrueck (DE)

(73) Assignee: Roche Diagnostics Corporation, Indianapolis, IN (US)

( * ) Notice: Subject to any disclaimer, the term of this patent is extended or adjusted under 35 U.S.C. 154(b) by 1035 days.

(21) Appl. No.: 10/398,493

(22) PCT Filed: Oct. 5, 2001

(86) PCT No.: PCT/EP01/11500

§ 371 (c)(1), (2), (4) Date: Apr. 4, 2003

(87) PCT Pub. No.: WO02/31177

PCT Pub. Date: Apr. 18, 2002

(65) Prior Publication Data

US 2004/0034197 A1 Feb. 19, 2004

(30) Foreign Application Priority Data

Oct. 7, 2000 (DE) .................... 100 49 673

(51) Int. Cl.
*C07K 14/00* (2006.01)
(52) U.S. Cl. .................... 530/350; 514/2
(58) Field of Classification Search ............. None
See application file for complete search history.

(56) References Cited

FOREIGN PATENT DOCUMENTS

| WO | WO 92/02615 | 2/1992 |
|----|-------------|--------|
| WO | WO 94/18329 | 8/1994 |

OTHER PUBLICATIONS

Günther et al., "Trypsin-specific acyl-4-guanidinophenyl esters for alpha-chymotrypsin-catalysed reactions", Eur. J. Biochem. 267: 3496-3501 (2000).*

Graf et al., "Selective Alteration of Substrate Specificity by Replacement of Aspartic Acid-189 with Lysine in the Binding Pocket of Trypsin", Biochemistry 26: 2616-2623 (1987).*
NCBI Protein sequence for P00763 (Downloaded Jul. 23, 2007).*
Xu, et al. "*Enzymatic Coupling of Specific Peptides at Nonspecific Ligation Sites: Effect of Asp189Glu Mutation in Trypsin on Substrate Mimetic-Mediated Reactions*" J. Org. Chem. (2001) 66: pp. 1627-1632.
V. Cerovsky and F. Bordusa, "*Protease-catalyzed fragment condensation via substrate mimetic strategy: a useful combination of solid-phase peptide synthesis with enzymatic methods*" Journal of Peptide Research (2000) 55: pp. 325-329.
Cervosky et al., "Semisynthesis of Ht31(493-515): Involvement of PKA-Anchoring Proteins in the Regulation of the cAMP-Dependent Chloride Current in Heart Cells" Chembiochem (2000) 2: pp. 126-129.
F. Bordusa, "*Nonconventiional amide bond formation catalysis: programming enzyme specificity with substrate mimetics*" Braz J. Med. Biol. Research (2000) 33: pp. 469-485.
Hans-Dieter Jakubke, "*Peptide Ligases—Tools for Peptide Synthesis*" Angew. Chem. Int. Ed. Engl. (1995) 34: pp. 175-177.
Kurth et al., "Engineering the S1' Subsite of Trypsin: Design of a Protease Which Cleaves between Dibasic Residues" Biochemistry (1998) 37: pp. 11434-11440.
Grunberg et al., "*European Journal of Biochemistry*" Dec. 2000, 267 pp. 7024-7030.
Briand, FEBS Letters, (1999) 442:43-47.
Hedstrom, et al., "Converting Trypsin to Chymotrypsin: The Role of Surface Loops", Reports, Mar. 6, 1992, pp. 1249-1253.

* cited by examiner

*Primary Examiner*—Anand U Desai
(74) *Attorney, Agent, or Firm*—McDonnell Boehnen Hulbert & Berghoff LLP

(57) ABSTRACT

The method for producing peptides, peptide mimetics and proteins is characterized in that an enzyme is used as a biocatalyst together with a peptide mimetic. The native specificity of the enzyme is modified by chemical or genetic manipulation, the substrate mimetic is a carboxyl component with an ester leaving group whose specificity determinant is adapted to the recognition site of the enzyme. The invention also concerns the trypsin variant D189K,K60E and its use as a C-N ligase in segment condensations.

2 Claims, 1 Drawing Sheet

METHOD FOR SYNTHESIZING PEPTIDES, PEPTIDE MIMETICS AND PROTEINS

Figure 1:
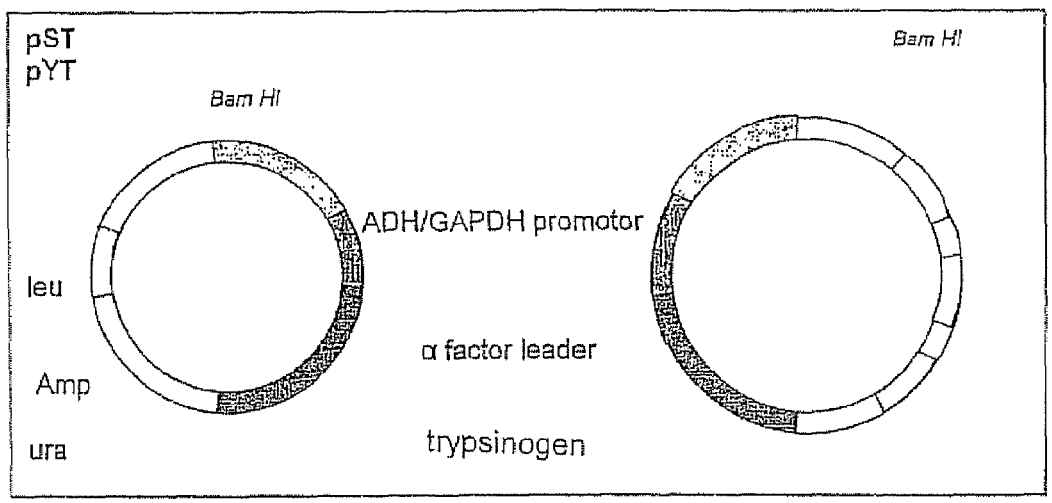

The invention concerns a method for synthesizing peptides, peptide mimetics and proteins by using an enzyme whose specificity has been changed in such a manner that it has been adapted to the structure of the ester leaving group.

The synthesis of peptides, peptide mimetics and proteins is becoming increasingly important for the systematic study of structure-function relationships in proteins as functional gene products and is making important contributions to the discovery of new effective therapeutic agents (cf. H. -D. Jakubke, "Peptide: Chemie und Biologie, Spektrum Akademischer Verlag, Heidelberg, Berlin, Oxford, 1996). The design of peptide ligases (H. -D. Jakubke, Angew. Chem. 1995, 107, 189) i.e. of enzymes which are able to catalyse the selective and irreversible linkage of two peptide segments by means of a specific peptide bond, has been a major challenge since nature has not yet been able to develop such an enzyme during the course of evolution. An important reason for this is the non-verifiable, extremely high demand on specificity since such a universal CN ligase must be able to molecularly recognize all possible combinations of the 21 proteinogenic amino acids that can occur statistically in the C- and N-terminal position of the peptide segments to be linked in order to catalyse a selective irreversible ligation. Nature therefore selected a stepwise protein synthesis in the cell from the N- to the C-terminus catalysed by peptidyl transferase which is very probably a very old ribozyme in evolution (B. Zhang, T. R. Cech, Nature 1997, 390, 96) where the specificity recognition of the amino acids to be linked is mainly achieved by codon-anticodon interaction and by a prior catalysis by highly specific aminoacyl tRNA synthetases.

Although in principle the reverse catalysis potential of peptidases (cf. among others W. Kullmann, Enzymatic Peptide Synthesis, CRC Press, Boca Raton, 1987; H.-D. Jakubke, Enzymatic Peptide Synthesis, in: The Peptides, Analysis, Synthesis, Biology, vol. 9, (eds.: S. Udenfriend, J. Meienhofer), Academic Press, New York, 1987, chapter 3) could be used to enzymatically link peptide segments under special circumstances, it would neither guarantee the irreversibility of the linked special peptide bond nor would it, a priori, exclude undesired proteolytic cleavage in the segments to be cleaved or in the final product if they contain potential cleavage sites for the peptidase that is used. Although it has been possible to improve the catalytic potential for peptide bond linkage by reengineering various peptidases e.g. subtilisin which has also been demonstrated by highly demanding fragment condensation (cf. among others D.Y. Jackson et al., Science 1994, 266, 243), the aforementioned disadvantages still apply.

Catalytic antibodies (cf. among others P. G. Schultz, R. A. Lerner, Science 1995, 269, 1835; G. MacBeath, D. Hilvert, Chem. Biol. 1996, 3, 433; D. B. Smithrub et al., J. Am. Chem. Soc. 1997, 119, 278) also have CN ligase activity as do synthetic peptide ligases based on a coiled-coil motif of GCN4 (K. Severin et al., Nature, 1997, 389, 706) or on a peptide template consisting of a strongly acidic coiled-coil peptide (S.Yao, J. Chmielewski, Biopolymers 1999, 51, 370) but although these are all interesting approaches for designing peptide ligases, they require special conditions for the ligations and hence their general application is extremely limited.

Methods based on the concept proposed many years ago of molecular clips for chemical CN ligations (T. Wieland et al., Annalen 1953, 583, 129; M. Brenner et al., Helv. Chim. Acta 1957, 40, 1497) such as amine and thiol capture (D. S. Kemp et al., J. Org. Chem. 1975, 40, 3465; N. Fotouhi et al., J. Org. Chem. 1989, 54, 2803), natural chemical ligation (M. Schnölzer, S. B. H. Kent, Science 1992, 256, 221; P. E. Dawson et al., Science 1994, 266, 776) and also the aldehyde method (C.-F. Liu, J. P. Tam, Proc. Natl. Acad. Sci. USA 1994, 91, 6584) require very special N- or C-terminal amino acid residues and hence they can only be used if specific sequences are present. In the case of native chemical ligation a synthetic peptide with a C-terminal thioester group is linked with a second peptide or protein which has to contain an N-terminal cysteine residue. Knowledge about protein splicing (cf. Review: C. J. Noren et al., Angew. Chem. 2000, 112, 458) was used to further develop native chemical ligation to intein-mediated protein ligation (expressed protein ligation, EPL) (T. W. Muir et al., Proc. Natl. Acad. Sci. USA 1998, 95, 6705; G. J. Cotton et al., J. Am. Chem. Soc. 1999, 121, 1100) in which the thioester group of the carboxy component from a recombinant protein that is fused with a cleavage-competent intein is formed by thiolytic cleavage on a column. The disadvantage of the necessity of an N-terminal cysteine residue at the N-terminus of the amino component for the ligation was of course not eliminated by this means. The thioester which forms as a result of the thiolytic cleavage on the column using 2-mercaptoethanesulfonic acid or thiophenol can be attacked nucleophilically not only after the reesterification but directly by the terminal α-amino group of the added amino components and hence a partial epimerization of the C-terminal amino acid residue cannot be excluded.

The object of the invention is the rational and evolutive design of enzyme variants having a specificity which is specially adapted to substrate mimetic structures while also having a significantly reduced proteolytic activity towards peptides and proteins.

This object is achieved by a method for producing peptides, peptide mimetics and proteins in which the specificity of an enzyme used in the synthetic process as a biocatalyst is changed such that it is adapted to the structure of the ester leaving group which is achieved by a chemical or rational or evolutive genetically engineered change in the enzyme that is directed towards the specificity-determining or catalytically important amino acid residues of the enzyme in such a manner that the resulting artificial C- N ligase recognizes the specificity determinants in the leaving group of the substrate mimetic as a molecularly and catalytically important region and such that bonds between the amino acid building blocks are linked.

BREIF DECRIPTION OF THE DRAWING

FIG. 1 is a map of the plasmids pST (5.4 kb) and pYT (14 kb) with the corresponding cleavage sites.

According to the present invention artificial C-N ligases are designed, contrary to the prevailing opinion of experts, by adapting the specificity of an enzyme to the structure of the ester leaving group. This can be achieved by a chemical as well as by a rational or evolutive genetically engineered change in the enzyme which can involve the specificity-determining enzyme binding regions or primarily only a few specific binding regions or catalytically important amino acid residues of the enzyme. The specificity determinant in the leaving group of the substrate mimetic then constitutes the molecular and catalytically productive recognition region for the artificial CN ligase such that bonds between the amino acid building blocks are no longer cleaved but are linked. The terms leaving group and specificity determinant are known to a person skilled in the art (F. Bordusa, Braz. J. Med. Biol. Res. 72 (2000) 469-485).

The findings of the invention are very surprising since after biocatalytic linkage of the CN bond by the inventive method, the peptidase is no longer able to recognize the synthesized CN bond nor any other CN bonds as a substrate because the specific ester leaving group is no longer present in the synthesized product and hence enzymatic cleavage can be ruled out.

Peptidase variants as well as members of other enzyme classes and subclasses such as esterases are preferably used for the inventive design.

The resulting peptides and proteins can be separated and purified by the usual methods of peptide and protein chemistry.

Proteolytically inactive peptide ligases, in particular peptidase variants and for example esterase variants, which act as biocatalysts for substrate mimetic-mediated peptide synthesis can be produced from native proteases by genetic engineering and in particular by means of three strategies. The first is the direct manipulation of the substrate specificity with the primary goal of generating enzyme specificities adapted to the substrate mimetic. This should inevitably always lead to a reduction of the native specificity when the structure of the substrate mimetic is different from the structure of the specific amino acid (Arg and Lys in the case of trypsin). In this connection the replacement of Asp 189 by basic residues is for example particularly promising. It has been known for a long time that Asp 189 is responsible for the Arg/Lys specificity of the enzyme and thus constitutes the most important amino acid residue for the native specificity of trypsin (L. Graf et al., Proc. Natl. Acad. Sci. USA, 1988, 85, 4961; L. B. Evnin et al., Proc. Natl. Acad. Sci. USA, 1990, 87, 6659). Replacing Asp 189 by His, Lys and Arg thus leads to an artificial specificity of trypsin for aromatic or aliphatic structures with a negative carboxylate group such as 4-carboxyphenyl, 4-carboxybenzyl, 3-carboxyethyl ester or even amino acid esters of 5-hydroxy-indole-2-carboxylic acid to name only a few suitable substrate mimetics for these peptide ligases. In contrast amino acid side chains of proteinogenic amino acids hardly fit productively into the modified binding pocket. As a consequence the rate of proteolysis is considerably less than that of the wild-type enzyme or negligible. Moreover a combination of these mutations with additional mutations in the S' region of trypsin (enzyme region on the C-terminal side of the cleavage or ligation site) leads to proteolytically inactive peptide ligases which is always the case when this mutation increases the specificity for the leaving group of the substrate mimetic. Thus the mutation K60E of the trypsin double mutant D189K, K60E results in a shift of the binding of 4-guanidinophenyl ester from the S1 into the S1' binding site of the enzyme. Such a shift has also been found for the previous cleavage-sensitive amino acids Lys and Arg. However, while the latter only leads to an unproductive binding, which does not result in a cleavage, the substrate mimetic is productively adapted and leads to synthesis.

In addition to direct manipulation of enzyme specificity, it is also possible to substitute amino acids in the catalytic triad of the enzyme (in the case of trypsin: His75, Asp102 and Ser195). It is known that in contrast to (activated) ester bonds or activated amide bonds e.g. in peptide 4-nitroanilides, the protonation of the amino function of the cleaved bond is essential for the cleavage of peptide bonds in addition to the increased nucleophilicity of the OH function of the active Ser195 (A. Fersht, Enzyme Structure & Mechanism, $2^{nd}$ ed. W.H. Freeman & Co., New York, 1984). Thus the substitution of Asp102 and/or His57 results in a discrimination of the enzyme between esterase and amidase activity even in the substrate mimetic-mediated reactions. A similar effect on the proteolytic activity would also be conceivable for the substitution of the active Ser195 by Thr or Cys.

Finally the third strategy consists of studying the indirect manipulation of enzyme activity with the aim of stabilizing zymogen-like and thus proteolytically inactive enzyme conformations (zymogens are the naturally occurring precursor enzymes of proteases which are, however, proteolytically inactive). Whereas the "real" zymogen trypsinogen Lys15Gly (cleavage of the Lys15-Ile16 bond leads to conversion of trypsinogen into active trypsin) has no peptide ligase activity, zymogen-like enzyme species do indeed have a peptide ligase character. Zymogen-like enzyme species are for example the enzyme variant Asp194Asn (Asp194 stabilizes the active enzyme conformation by forming a salt bridge with the N-terminus of the activated trypsin) and also the variant Cys191Ala (Cys191 stabilizes the active enzyme by forming a disulfide bridge).

The present invention also concerns a method for producing essentially proteolytically inactive peptide ligases, in particular trypsin variants, by genetic engineering. The desired mutation is introduced starting with vectors containing the protease-coding sequence, for example the trypsin-coding or trypsinogen-coding sequence. For example it is possible to use the *E. coli* vector pST, a yeast shuttle vector with a ADH/GAPDH promoter and an α factor leader sequence which is fused to the trypsinogen-coding sequence (L. Hedstrom et al., Science 255 (1992) 1249). Afterwards the new vector is transformed in a suitable host such as *E. coli*. If necessary the modified protease sequence such as a modified trypsin or trypsinogen sequence can be subcloned in suitable expression vectors such as the yeast vector pYT. If the mutation occurs directly with an expression vector, this additional step can be omitted. Afterwards the protease variant is expressed in the host cell such as in *E. coli* or yeast. The modified protease variant such as the modified trypsin or its zymogen is isolated by suitable protein-biochemical methods such as ion exchange chromatography. If the protease variant is for example a zymogen e.g. a trypsinogen variant, it is activated in the usual manner by converting the zymogen variant into the protease variant for example by proteolytic cleavage. If necessary this can be followed by further purification steps e.g. by means of affinity chromatography (if binding to SBTJ is still possible after the modification) or by means of perfusion chromatography. Finally the protease variant is dialysed if necessary against a suitable buffer and concentrated.

The principle of the present invention is illustrated by the trypsin variant D189K,K60E [SEQ ID NO: 1] and its use as a CN ligase in a segment condensation. In this trypsin mutant the amino acid D at position 189 is replaced by K and the amino acid K at position 60 is replaced by E. The sequence of the trypsin wild-type is known to a person skilled in the art. The trypsin species D189K, K60E [SEQ ID NO: 1] was developed specially for recognizing the 4-guanidinophenyl ester leaving group. The charge reversal in the primary specificity-determining S1 binding pocket due to the mutation D189K prevents binding of the amino acid residues Lys and Arg which were originally specific for trypsin. However, this mutation alone also leads to a significant reduction of the activity towards acyl-4-guanidinophenyl ester substrate mimetics. An additional substitution of Lys60 by Glu according to the invention results in the formation of a new binding pocket in the S1' binding site region of the enzyme which is specific for the 4-guanidinophenyl ester leaving group which is surprising to a person skilled in the art. The result is a significant increase in the specificity for acyl-4-guanidinophenyl esters whereas its unspecificity for the originally specific amino acid residues remains. The trypsin variant D189K,K60E [SEQ ID NO: 1] is used to prepare peptides, peptide mimetics and proteins. The choice of the buffer system, the reaction time and other parameters such as the reaction temperature etc. is relatively uncritical and can be simply determined by a person skilled in the art of enzymatic transformations.

An acyl-4-guanidinophenyl ester such as a peptide-4-guanidinophenyl ester is used as the carboxyl component and another peptide or peptide mimetic is used as the amino component for the production of peptides, peptide mimetics and proteins. The desired complete peptide, peptide mimetic or protein is formed by ligating the amino component and the carboxyl component. Surprisingly this type of synthesis does not lead to a modification of functional amino acid side chains of trifunctional amino acids such as lysine nor to a detectable proteolytic cleavage of the reactants or of the ligation product.

The synthesis of the biologically active Ht31 (493-515) peptide described in the following confirms the irreversible ligase character of the substrate mimetic-specific trypsin variant based thereon.

EXAMPLE 1

Production of the Trypsin Mutant D189K,K60E

Plasmids

The *E. coli* vector pST was used for the site-directed mutagenesis. This contains a part of the Bluescript vector and the gene for anionic rat trypsin which is fused with an α-factor leader and with an ADH/GAPDH promoter.

The protein was expressed with the aid of the pYT plasmid, a pBS24 derivative which carries the selection marker for uracil- and leucine-deficient medium.

The pST as well as the pYT plasmid have an ampicillin resistance gene. The maps of both vectors i.e. of the plasmids pST (5.4 kb) and pYT (14 kb) with the corresponding cleavage sites are shown in FIG. 1.

Mutagenesis

Site-directed mutageneses were carried out using the Quik change® kit (STRATAGENE) in the *E. coli* plasmid pST.

The procedure was like that of a PCR in which both plasmid strands of the pST vector are replicated by PFU polymerase starting with two synthetic oligonucleotide primers which contain the desired mutation. Wild-type pST served as the template to generate single mutations. These single mutants were again the starting point for constructing the double mutants.

The following oligonucleotide primers were used in which the letters in bold type indicate the mutations:

```
D189K    a)   5'-GGA GGC AAG AAC GAT TGC TGC-3'
              [SEQ ID NO: 2]

b)   5'-GCA GGA ATC GTT CTT GCC TCC-3'
              [SEQ ID NO: 3]

K60E     a)   5'-CAC TGC TAT GAG TCC CGC ATC-3'
              [SEQ ID NO: 4]

b)   5'-GAT GCG GGA CTC ATA GCA GTG-3'
              [SEQ ID NO: 5]
```

The resulting PCR product was transformed into ultracompetent *E. coli* XL II blue cells (STRATAGENE). Subsequent selection was carried out on nutrient agar plates containing ampicillin (LB-amp). The picked colonies were transferred to a liquid medium containing ampicillin (LB-amp) and the plasmid was isolated using the SNAP-kit (INVITROGENE) after 1 day of culture. The isolated DNA was checked by electrophoresis using a 1% agarose gel. By sequencing the complete gene it was possible to ensure that only the desired mutations were present.

Subcloning

A subcloning in the pYT expression vector was necessary for all mutants that were generated in the pST plasmid. This was carried out by restriction digestion with Bam HI and Sal I and ligation into the corresponding pYT vector fragment. All vector fragments were transferred in the appropriate restriction mixture to a low melting agarose gel (0.8%) and cut out after adequate separation. The gel pieces were melted at 55° C. and pooled according to the desired combination and ligated at 16° C. overnight with T4 DNA ligase. The transformation and plasmid isolation which was again necessary was carried out as described above.

Successful subcloning was tested by means of a characteristic restriction pattern after double digestion with Eco RI and Bam HI in the agarose gel.

By sequencing the complete trypsinogen gene it was possible to ensure that only the desired mutations were present.

Yeast Transformation and Selection

The yeast cell strain that was used is designated *Saccharomyces cerevisiae* DLM 101α [Mat a,leu 2-3,-112 his 2, 3-11, -15 can 1, ura 3Δ, pep4Δ, [cir⁰], DM 23]. The EZ yeast transformation kit (ZYMO research) was used to prepare competent yeast cells and to transform the pYT plasmids. The selection was carried out on uracil-deficient SC plates by incubation at 30° C. for 3 to 4 days. Leucine-deficient SC plates were inoculated with individual colonies and also incubated for 3 to 4 days at 30° C. which led to an increase in the copy number of the plasmid in the cells. Individual colonies of these plates were used to inoculate precultures of the leucine-deficient SC liquid medium containing 8% glucose. They were incubated by shaking at 30° C. and 120 rpm for 3 days. 20 ml preculture was used as the inoculum to inoculate the 1 litre main cultures containing YPD medium (1% glucose, 1% bactopeptone, 0.5% yeast extract). The incubation parameters corresponded to those of the preculture and they were harvested after 4 days.

Isolation and Purification of the Trypsin Variants

The cells were firstly separated by centrifuging for 20 min at 4000 rpm and the supernatant was adjusted to pH 4.0 and again centrifuged at 12000 rpm. The almost particle-free supernatant containing trypsinogen was applied to a Toyopearl 650 M (SUPELCO) cation exchanger column equilibrated with 2 mM sodium acetate/100 mM acetic acid (pH 4.5). It was eluted by means of a linear pH gradient starting at 2 mM sodium acetate/100 mM acetic acid (pH 4.5) to 200 mM Tris/HCl (pH 8.0).

The fractions containing trypsinogen were determined by SDS polyacrylamide gel electrophoresis using a 15% polyacrylamide gel and pooled. The volumes of the protein solutions were concentrated to about 10 to 15 ml by means of Centriprep concentrators (AMICON).

Activation of the trypsinogen variant to the corresponding trypsin D189K+K60E was carried out using highly purified enterokinase (BIOZYME) at pH 6.5 and was monitored by SDS gel electrophoresis.

The activated enzyme was purified using a Biocad Sprint perfusion chromatography system (PERSEPTIVE BIOSYSTEMS). The protein samples were separated on a POROS 20 HQ—anion exchanger column (4×100 mm, PERSEPTIVE BIOSYSTEMS) equilibrated with 5% Bis/Tris propane pH 6.0 and by subsequent gradient elution up to 95% 3 M NaCl solution. The fractions containing trypsin were examined with the aid of an SDS gel and pooled. They were subsequently dialysed against 1 mM HCl at 4° C. and the samples were concentrated with Centriprep concentrators to 2 to 4 ml.

The final yields were about 2 to 5 mg protein per litre culture medium.

Determination of the Concentration

The protein concentration of the preparations was determined according to the method of Bradford on a spectrophotometer at a wavelength of 595 nm. The calibration curve was plotted on the basis of a serial dilution of bovine trypsin between 50 μm/ml and 1 mg/ml.

EXAMPLE 2

Synthesis of Ht31 (493-515) by Means of the Trypsin Variant D189K, K60E

The target molecule H-Asp-Leu-Ile-Glu-Glu-Ala-Ala-Ser-Arg-Ile-Val-Asp-Ala-Val-Ile-Glu-Gln-Val-Lys-Ala-Ala-Gly-Ala-Tyr-OH (Ht31 (493-515)) [SEQ ID NO: 6] was synthesized by ligating the octapeptide-4-guanidinophenyl ester Boc-Asp-Leu-Ile-Glu-Glu-Ala-Ala-Ser-OGp [SEQ ID NO: 7] (2.2 mg, ca. 0.001 mmol) used as a carboxy component with the peptide H-Arg-Ile-Val-Asp-Ala-Val-Ile-Glu-Gln-Val-Lys-Ala-Ala-Gly-Ala-Tyr-OH (1 mg, ca. 0.0005 mmol) acting as an amino component. An aqueous buffer system containing 40% organic solvent was used as the solvent. After adding both reactants, the reaction was started by adding the trypsin variant D189K,K60E [SEQ ID NO: 1] and analysed after complete conversion of the carboxy component. The enzyme catalysis led to a complete acylation of the amino component. The identity of the synthesis product was checked by conventional methods of organic chemistry including amino acid analysis. The reaction neither modified the trifunctional amino acid side chains nor did it lead to a detectable proteolytic cleavage of the reactants or of the ligation product.

The invention claimed is:

1. Trypsin variant as set forth in SEQ ID NO: 1, which according to the chymotrypsin nomenclature is D189K, K60E.

2. The method of synthesizing the polypeptide H-Asp-Leu-Ile-Glu-Glu-Ala-Ala-Ser-Arg-Ile-Val-Asp-Ala-Val-Ile-Glu-Gln-Val-Lys-Ala-Ala-Gly-Ala-Tyr-OH as set forth in SEQ ID NO: 6 comprising mixing i) Boc-Asp-Leu-Ile-Glu-Glu-Ala-Ala-Ser-OGp (SEQ ID NO: 7), ii) H-Arg-Ile-Val-Asp-Ala-Val-Ile-Glu-Gln-Val-Lys-Ala-Ala-Gly-Ala-Tyr-OH (SEQ ID NO: 8), and iii) the trypsin variant as set forth in SEQ ID NO: 1, in an aqueous buffer system comprising 40% organic solvent, thereby ligating SEQ ID NO: 7 with SEQ ID NO: 8 using the trypsin variant, which results in the production of SEQ ID NO: 6.

* * * * *

SEQUENCE LISTING

```
<160> NUMBER OF SEQ ID NOS: 1

<210> SEQ ID NO 1
<211> LENGTH: 223
<212> TYPE: PRT
<213> ORGANISM: Artificial
<220> FEATURE:
<223> OTHER INFORMATION: Synthetic trypsin variant

<400> SEQUENCE: 1

Ile Val Gly Gly Tyr Thr Cys Gln Glu Asn Ser Val Pro Tyr Gln Val
1               5                   10                  15

Ser Leu Asn Ser Gly Tyr His Phe Cys Gly Gly Ser Leu Ile Asn Asp
            20                  25                  30

Gln Trp Val Val Ser Ala Ala His Cys Tyr Glu Ser Arg Ile Gln Val
        35                  40                  45

Arg Leu Gly Glu His Asn Ile Asn Val Leu Glu Gly Asn Glu Gln Phe
    50                  55                  60

Val Asn Ala Ala Lys Ile Ile Lys His Pro Asn Phe Asp Arg Lys Thr
65                  70                  75                  80

Leu Asn Asn Asp Ile Met Leu Ile Lys Leu Ser Ser Pro Val Lys Leu
                85                  90                  95

Asn Ala Arg Val Ala Thr Val Ala Leu Pro Ser Ser Cys Ala Pro Ala
            100                 105                 110

Gly Thr Gln Cys Leu Ile Ser Gly Trp Gly Asn Thr Leu Ser Ser Gly
        115                 120                 125

Val Asn Glu Pro Asp Leu Leu Gln Cys Leu Asp Ala Pro Leu Leu Pro
    130                 135                 140

Gln Ala Asp Cys Glu Ala Ser Tyr Pro Gly Lys Ile Thr Asp Asn Met
145                 150                 155                 160

Val Cys Val Gly Phe Leu Glu Gly Gly Lys Lys Ser Cys Gln Gly Asp
                165                 170                 175
```

```
Ser Gly Gly Pro Val Val Cys Asn Gly Glu Leu Gln Gly Ile Val Ser
            180             185                 190

Trp Gly Tyr Gly Cys Ala Leu Pro Asp Asn Pro Gly Val Tyr Thr Lys
        195             200             205

Val Cys Asn Tyr Val Asp Trp Ile Gln Asp Thr Ile Ala Ala Asn
    210             215             220
```